Figure 1:
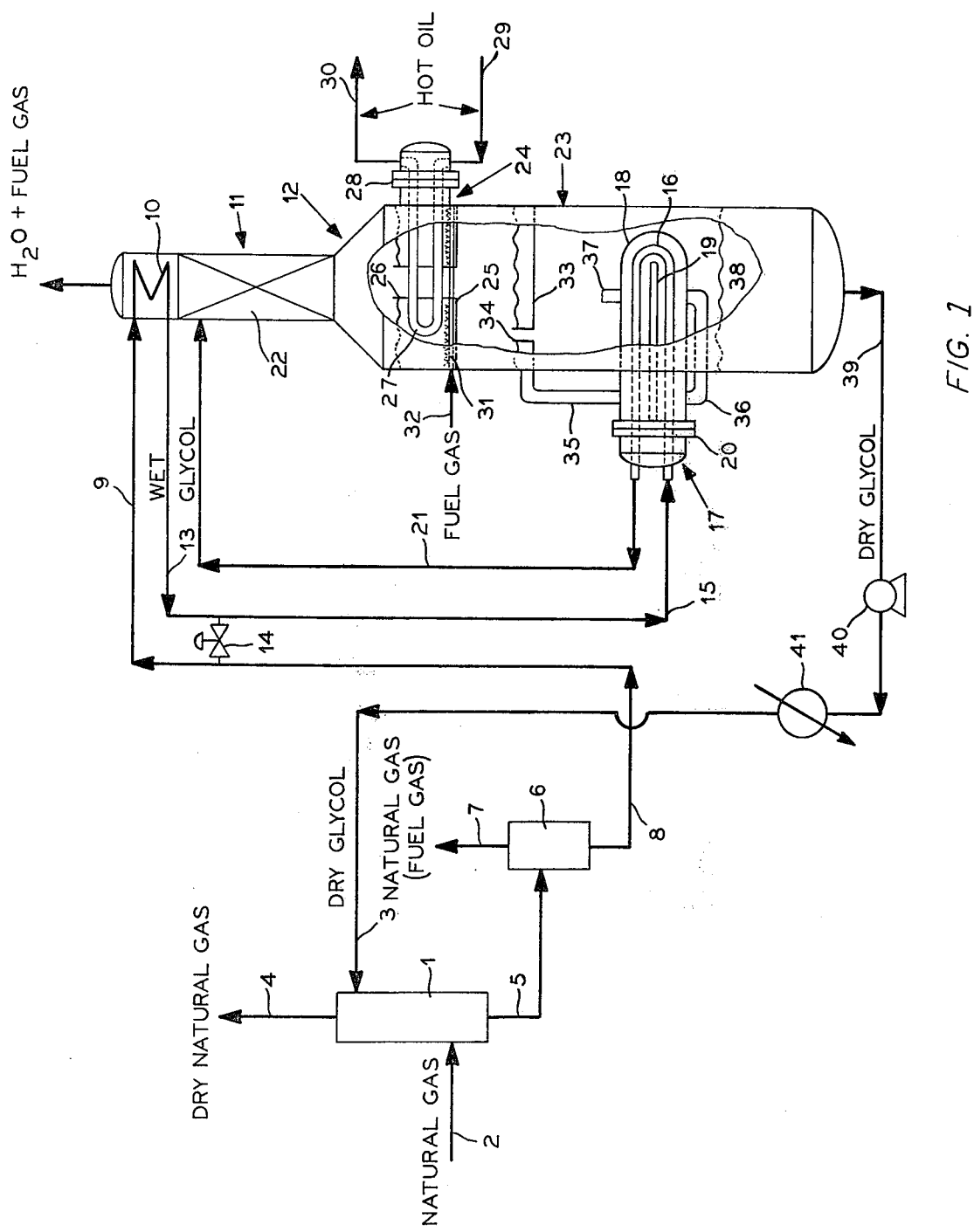

United States Patent [19]

Moyer

[11] 4,010,009
[45] Mar. 1, 1977

[54] GLYCOL REGENERATION
[75] Inventor: G. A. Moyer, Bartlesville, Okla.
[73] Assignee: Phillips Petroleum Company, Bartlesville, Okla.
[22] Filed: Nov. 21, 1975
[21] Appl. No.: 634,107
[52] U.S. Cl. .................................... 55/32; 55/171
[51] Int. Cl.² ...................................... B01D 53/14
[58] Field of Search ............... 55/31, 32, 171–177; 159/31; 165/132

[56] References Cited
UNITED STATES PATENTS

| | | | |
|---|---|---|---|
| 3,105,748 | 10/1963 | Stahl | 55/32 |
| 3,234,108 | 2/1966 | Hull | 55/32 X |
| 3,237,684 | 3/1966 | Morgan | 165/132 X |
| 3,254,473 | 6/1966 | Fryar et al. | 55/32 |
| 3,321,890 | 5/1967 | Barnhart | 55/32 |
| 3,397,731 | 8/1968 | Gravis et al. | 159/31 X |
| 3,451,897 | 6/1969 | Welch | 159/31 X |
| 3,616,598 | 11/1971 | Foral, Jr. | 55/171 X |
| 3,688,839 | 9/1972 | Kirschner | 165/132 X |
| 3,844,736 | 10/1974 | Kruis et al. | 55/32 |

Primary Examiner—Charles N. Hart
Assistant Examiner—Robert H. Spitzer

[57] ABSTRACT

In a regenerator vessel for stripping water from wet glycol, a tray is provided for collecting dry glycol; from that tray the dry glycol flows by gravity only through an indirect heat exchanger into indirect heat exchange relationship with the incoming wet glycol. A process for drying wet gas such as water-containing natural gas includes glycol regeneration with the gravity flow of the dry glycol through heat exchange means.

14 Claims, 1 Drawing Figure

GLYCOL REGENERATION

The present invention relates to a glycol regeneration. In accordance with one of its more specific aspects, this invention relates to the drying of water-containing gas using glycol as a desiccant. A further aspect of this invention relates to the regeneration of the wet glycol produced. Another aspect of this invention relates to a glycol regenerator.

BACKGROUND OF THE INVENTION

Wet gases, e.g., water-containing natural gas, can be effectively dried by contacting them with a desiccant, e.g., with dry alkylene glycol. In this well known process, a dry gas stream and a wet desiccant stream is produced. It is furthermore known in the art that the wet desiccant stream can be regenerated by passing this stream through a regenerator or a stripping column to remove the acquired moisture. The regenerated desiccant can be recycled and used for further water removal from the gas.

It is also known in the art that the desiccant can be passed through heat exchange coils, which are located in the bottom of the stripper vessel. In this known process, the water-containing desiccant is passed through stagnant desiccant. The heat exchange of this known process is thus not optimal.

THE INVENTION

It is thus one object of this invention to provide a new desiccant regenerator.

Another object of this invention is to provide a desiccant regenerator which effectively utilizes a portion of the heat introduced into the wet desiccant in order to remove the water therefrom in the regenerator.

A further object of this invention is to provide a desiccant regenerator which is simple in construction, easy to maintain, and provides a heat exchange between the incoming wet desiccant and the hot dry desiccant that can be serviced without shutting down the regenerator.

A further object of this invention is to provide a process for drying water-containing gas.

These and other objects, features, details, embodiments and advantages of this invention will become apparent to those skilled in the art from the following detailed description of the invention, the appended claims, and the drawing which schematically shows an apparatus for drying gas, including a desiccant regenerator partially broken open and in cross section to show the interior features thereof.

In order to design oil and gas processing facilities, it is desirable to provide a desiccant regenerator with minimum space requirements, which in addition is easy to service and maintain. This is particularly desirable and constitutes a specific problem solved by the present invention for gas and oil processing facilities in offshore installations. In such installations platform space is very limited and labor and operating costs are multiplied by the difficult conditions prevailing.

In accordance with this invention, I have now provided a desiccant regenerator comprising a regenerator vessel, first means for introducing wet desiccant into the upper portion of the regenerator vessel, second means for withdrawing of $H_2O$ overhead from the upper portion of the regenerator vessel, third means for withdrawing of dry desiccant from the lower portion of the vessel, fourth means to reboil wet desiccant, a collecting tray inside of said regenerator vessel for collecting hot dry desiccant before it reaches said third means, indirect heat exchange means, a first fluid conduit establishing a fluid connection between the collecting tray and the heat exchange means so that the dry desiccant flows by gravity only from the collecting tray through the heat exchanger, a second fluid conduit establishing a fluid connection between a source of wet desiccant and the heat exchanger, a third fluid conduit establishing a fluid connection between the heat exchanger and the first means for introducing wet desiccant into the regenerator vessel.

More specifically and in accordance with one embodiment, the indirect heat exchanger comprises a first inlet and a first outlet of a first flow pattern being arranged at a lower elevation than said collecting tray, further comprising a second inlet and a second outlet of a second flow pattern, said two flow patterns being separated and arranged such that heat is exchanged indirectly between the fluids flowing through said patterns at different temperatures, the first fluid conduit being connected to the first inlet and the collecting tray, the second fluid conduit being connected to the second inlet and the source of wet desiccant and the third fluid conduit being connected to the second outlet and the first means for introducing wet desiccant into the regenerator.

The important feature of this invention consists in the provision of an indirect heat exchange means between hot, dry desiccant and incoming cool, wet desiccant in which the two, e.g., countercurrently flowing streams, come into efficient heat exchange relationship without the use of a pump.

The heat exchange means, in accordance with a preferred embodiment of this invention, are essentially completely located inside of the regenerator vessel. This embodiment of the invention is advantageous both for saving space and for saving insulating material for the heat exchanger. The heat exchanger of this embodiment preferably consists essentially of an elongated shell with a longitudinal partition wall defining, e.g., the first flow pattern, e.g., for the hot, dry desiccant and coils extending along the one side of the partition wall and returning on the other side of the partition wall. Thereby, essentially a countercurrent flow of the hot and cold desiccant streams can be achieved resulting in a very efficient heat exchange. The further advantage of the construction just described is that the coils or tubes can be removed from the shell without shutting down the regenerator vessel because the longitudinal shell of the heat exchanger separates the interior of the regenerator vessel from the outside.

In order to prevent an accumulation of air in the gravity flow pattern of the heat exchanger, it is presently preferred to provide a fourth conduit connected to the first outlet, which conduit extends into an elevation above the first flow pattern of the heat exchanger. This embodiment assures that, even though the flow of hot, dry desiccant through the first flow pattern of the heat exchanger ceases for a while, the flow pattern still remains full of liquid desiccant.

For the embodiment just described, it is particularly advantageous to have the fourth conduit end at a level above the first flow pattern inside of the regeneration vessel. The dry desiccant leaving the first flow pattern of the heat exchanger then overflows out of the end of the fourth conduit and accumulates in the lower portion of the regenerator vessel.

A reflux is generated in accordance with a further embodiment of this invention in the regenerator vessel by arranging a reflux generating conduit in the upper portion of the regenerator vessel above the locus of introduction of wet desiccant into the regenerator vessel. This reflux conduit constitutes a part of the second conduit mentioned above. Evaporated water and some desiccant condensates on the reflux generating conduit, thus producing a reflux stream of water and some desiccant inside of the regenerator vessel.

The means to reboil wet desiccant is conveniently located inside of the regenerator vessel at an elevation between the first means and the collecting tray. This reboiler comprises a chimney tray constituting a partition with an overflow riser in the regenerator vessel. On this chimney tray, the desiccant is boiled and overflowing hot stripped desiccant from the chimney tray flows to the collecting tray. The fact that the hot stripped desiccant is accumulated on a collecting tray in accordance with this invention has the further advantage that the residence time of the stripped desiccant is increased so that the hot dry desiccant is more effectively degased before it flows by gravity flow through the indirect heat exchanger described above.

The heating of the liquid desiccant accumulating on the chimney tray can be achieved by any convenient means. Presently preferred is to heat the liquid desiccant by passing a hot liquid, such as hot oil through a heating coil arranged on the chimney tray.

In order to generate an increased turbulence in the boiling liquid desiccant on the chimney tray, and in order to increase the heat exchange efficiency between the heating element on the chimney tray and the liquid desiccant, it is presently preferred to sparge gas, such as fuel gas, through the desiccant on the chimney tray. This fuel gas leaves the regenerating vessel together with $H_2O$ vapor overhead through the top of the regenerator vessel.

The presently preferred regenerator vessel comprises a wide bottom section and a narrower top section. In the narrower top section, a distillation column packing is arranged. The collecting tray is arranged above the center line of the bottom section underneath the column packing and under the chimney tray. The wet desiccant is introduced into the area of the top section, which is filled with the distillation column packing, whereas the reflux generating conduit is arranged above this distillation column packing.

A further important aspect in accordance with still another embodiment of this invention resides in the sequence of pumping and cooling the regenerated desiccant. A pump for generating high pressure desiccant is provided for, pumping the hot desiccant from the bottom of the regenerator vessel to a contactor. Downstream of this pump the desiccant is passed through a water cooler. This arrangement has the further advantage over pumping the precooled regenerated desiccant that the load on the pump is reduced, since a less viscous fluid has to be pumped.

The preferred embodiment of this regenerator thus is operated as follows: Dry hot desiccant is collected on an intermediate tray, passed by gravity flow only through an internal heat exchanger into indirect heat exchange with cold wet desiccant and into the bottom portion of the regenerator; the still hot dry desiccant then is passed through a pump and downstream thereof through a water cooler to the contactor. No heat exchange coils on the collecting intermediate tray, no external pump and cooler and no external heat exchanger are necessary before the dry desiccant reaches the bottom of the regenerator vessel. Furthermore, the horsepower demand of the pump feeding the dry desiccant to the contactor is reduced, since hot and not cooled desiccant is being pumped.

In accordance with still a further embodiment of this invention, there is provided a process for drying gas, which process comprises contacting the gas with a dry desiccant to produce a dry gas stream and a wet desiccant stream, regenerating the wet desiccant stream by passing it through a stripper to produce an $H_2O$ vapor stream and a dry desiccant stream, collecting the dry desiccant in the stripper at an intermediate level, passing the dry desiccant collected by gravity flow into indirect heat exchange relationship with the wet desiccant before it enters the stripper, and recovering the dry desiccant.

Whereas various desiccants can be used for the different drying purposes they are supposed to achieve, it is presently preferred, particularly for drying natural gas, to use a glycol as said desiccant. This glycol will generally be a straight-chain alkylene glycol, such as ethylene glycol, diethylene glycol, triethylene glycol, and tetraethylene glycol. The strong affinity of these glycols for water, as well as their good chemical and thermal stability, ready availability, and their reasonable price, constitute the main advantages of these desiccants. The higher boiling glycols, such as triethylene glycol and tetraethylene glycol, are presently preferred because they offer the further advantage of lower volatility, reduced loss of desiccant from the absorber, and greater dew point depression for the dehydrated gas.

Advantageously, and in accordance with a preferred embodiment of this invention, the recovered dry desiccant is recycled to the dehydrating step in which the dry desiccant is contacted with the wet gas.

For a plant operation, it is preferred to pass the wet desiccant after it has contacted and at least partially dehydrated the water-containing gas first through a flashing section in which the wet desiccant coming from a high pressure contacting zone is flashed by suddenly lowering its pressure, thereby evaporating gas that is dissolved in the wet desiccant. The degassed wet desiccant thereafter is passed to the regeneration as described.

A reflux of liquid desiccant is generated in the regenerator vessel, preferably by passing the wet desiccant through heat exchanger coils in the top section of the regenerator vessel. Water and some desiccant condenses on these coils generating a reflux in the stripper or regenerator vessel. The portion of the wet desiccant that has passed through these reflux generating coils thereafter is recombined with the rest of the wet desiccant and introduced into the stripper for regeneration.

In order to explain the invention in more detail, reference is now made to the drawing showing further preferred embodiments of this invention.

In a contactor 1, wet natural gas entering via line 2 is contacted with dry glycol entering the contactor 1 via line 3. Dry natural gas is removed from the contactor 1 via line 4. From the bottom of the contactor 1, wet glycol is removed via line 5.

The wet glycol 5 is passed into a flash tank 6 from which gas that is freed by the flashing operation from the wet glycol leaves via line 7. Wet glycol essentially free of natural gas leaves the flash tank 6 via line 8.

The wet glycol from line 8 is introduced via line 9 into heat exchanger coil 10 arranged in the top of the upper portion 11 of a glycol stripper 12. The wet glycol leaves the reflux generator coil 10 via line 13 and is introduced via line 15 into heat exchanger coil 16 of heat exchanger 17. A valve 14 is provided for so that some wet cold glycol can by-pass the reflux coil 10, if desired, for controlling the reflux. The heat exchanger 17 further comprises a shell 18 and a longitudinal dividing plate 19. The coil 16 is mechanically held in the shell 18 via a flange connection 20. The wet glycol leaves the heat exchanger 17 via line 21 and is introduced into a distillation column packing 22 arranged in the upper portion 11 of the glycol stripper 12. Liquid glycol is reboiled near the upper end of the lower section 23 of the glycol stripper 12 in a reboiler 24.

The reboiler 24 comprises a chimney tray 25 with an overflow riser 26. On this chimney tray 25 a heating coil 27 is arranged, which is removably attached to the regenerator by a flange connection 28. Hot oil can be introduced into the heating coil 27 via line 29, and the hot oil is removed via line 30. Desiccant on the chimney tray is evaporated by the reboiler. On the bottom of the chimney tray 25, a gas sparging pipe 31 is arranged via which, e.g., fuel gas can be bubbled through the boiling liquid glycol. The fuel gas is entered into the sparge pipe 31 via line 32.

Evaporated water and glycol passes through the distillation column packing 22 and contacts reflux condenser coils 10. Part of the water and some glycol condenses on these coils and provides a desirable reflux.

Part of the boiling glycol on the chimney tray 25 overflows the riser 26 and accumulates on a collector tray 33, which is provided with a small weir 34. The accumulated dry glycol flows from the collector tray 33 via a pipe 35 by gravity only into the shell 18 of the heat exchanger 17. The hot dry glycol flows around the longitudinal separator wall 19 and countercurrently contacts coil 16 carrying the wet cold glycol. The dry glycol leaves the heat exchanger 17 via conduit 36, which ends inside of the lower section 23 of the wet glycol stripper 12. Under normal operating conditions, pipe 35, as well as the heat exchanger 17, are dimensioned such that essentially all the dry hot glycol flows through the heat exchanger 17.

The end 37 of the conduit 36 is arranged above the heat exchanger shell 18. This arrangement assures that the shell 18 of the heat exchanger is always filled with glycol. The dry glycol leaving the end 37 of pipe 36 falls into the bottom of the lower section 23 of the stripper 12, where a reservoir 38 of liquid can accumulate. From this reservoir dry glycol is withdrawn via line 39. This dry glycol is repressured by a pump 40 and cooled by a cooler 41 so that it can be reintroduced via line 3 into the contacting zone 1.

To arrange the heat exchanger 17 essentially completely inside of the glycol stripper 12 is preferred, and brings about the considerable advantages of savings in outside space and mounting structure for the heat exchanger vessel and the elimination of the need of heat insulation of the heat exchanger 17. Only the head of this heat exchanger 17 and pipe 35 are heat insulated.

By providing block valves in the hot glycol lines 35 and 36 and a by-pass line for the cold wet glycol by-passing the heat exchanger, the heat exchanger 17 can be very conveniently serviced. The block valves (not shown in the drawing) are closed, and the heat exchanger can be opened at the flange connection 20, such as to remove the head of the heat exchanger with the coil 16 and the partition wall 19 attached thereto. Thus, the heat exchanger can be readily serviced without depressuring the glycol stripper 12. Riser 34 in this case serves as a glycol by-pass.

The invention will still be more fully understood from the following calculated example for a process for drying wet natural gas.

EXAMPLE

178 Million standard cubic feet per day (58.4 m³/s) of wet natural gas at 90° F (32° C) and 1330 psia (9.16 MPa) containing about 40 lb/MMSCF (0.64 gm/m³) of water are introduced into a dehydrating unit 1. In this dehydrating unit, the natural gas is contacted with about 32 gallons per minute (0.00202 m³/s) of substantially dry triethylene glycol. The triethylene glycol used is about 98.5 to 99.0 weight percent pure. Wet glycol from the bottom of the absorber 1 is flashed at about 115 psia (0.793 MPa) to remove most of the dissolved natural gas. This removed natural gas is used as fuel gas. Part of the wet glycol is used as coolant in the stripper condenser 10 to generate reflux. This wet glycol is combined with the remaining cold wet glycol and is heat exchanged with hot regenerated glycol overflowing from the reboiler chimney tray 25 via the accumulator tray 33. The hot regenerated dry glycol has a temperature of about 380° F (193° C). The wet glycol leaves the heat exchanger at a temperature of about 300° F (149° C). This preheated wet glycol is passed to the stripping section 22 of the regenerator 12. Dry glycol having a temperature of about 228° F (109° C) overflows the heat exchanger standpipe exit 37 and flows into the surge space at the bottom of wet glycol stripper 12 to produce a dry glycol reservoir 38.

The glycol heat exchanger duty is about 2.09 million Btu/hr (612 kJ/s.) The reboiler duty is about 3.0 million Btu/hr (879 kJ/s). The dry natural gas leaving the absorber 1 via line 4 contains about 6 lb of water per MMSCF of natural gas (0.096 gm/m³).

Reasonable variations and modifications, which will become apparent to those skilled in the art, can be made in this invention without departing from the spirit and scope thereof.

I claim:
1. A desiccant regenerator comprising
   a. a regenerator vessel having a dry desiccant reservoir in the lower portion thereof,
   b. first means for introducing wet desiccant into the upper portion of the regenerator vessel,
   c. second means for withdrawing H₂O from the upper portion of the regenerator vessel,
   d. third means for withdrawing of dry desiccant from said dry desiccant reservoir,
   e. fourth means to reboil desiccant,
   f. a collecting tray for collecting regenerated dry desiccant arranged
      aa. within said regenerator vessel, and
      bb. at an elevation between said fourth means to reboil the desiccant and said third means,
   g. an indirect heat exchanger arranged at a lower elevation than said collecting tray,
   h. a first fluid conduit establishing a fluid connection between said collecting tray and said heat exchanger so that the regenerated desiccant flows by gravity from the collecting tray through said first fluid conduit and said heat exchanger into indirect heat exchange with said wet desiccant before it is introduced into the regenerator vessel in step (b),
  i. a second fluid conduit establishing a fluid connection between a source of wet desiccant and said heat exchanger,
  j. a third fluid conduit establishing a fluid connection between said heat exchanger and said first means for introducing wet desiccant into said regenerator vessel, and
  k. a fourth fluid conduit establishing a fluid connection between said indirect heat exchanger and said dry desiccant reservoir so that the regenerated desiccant after the indirect heat exchange with the wet desiccant flows by gravity from the heat exchanger into said dry desiccant reservoir.

2. A regenerator in accordance with claim 1, the indirect heat exchanger of which comprises a first inlet and a first outlet of a first flow pattern being arranged at a lower elevation than said collecting tray, and a second inlet and a second outlet of a second flow pattern, said two flow patterns being separated and arranged such that heat is exchanged indirectly between fluids flowing through said patterns at different temperatures, and wherein said first conduit is connected to said first inlet, said second conduit is connected to said second inlet and said third conduit is connected to said second outlet.

3. A regenerator in accordance with claim 2 wherein said fourth conduit extends into said vessel and ends at an elevation above said first flow pattern of said indirect heat exchanger.

4. A regenerator in accordance with claim 1 wherein said indirect heat exchanger is arranged essentially completely inside of said regenerator vessel.

5. A regenerator in accordance with claim 1 comprising a reflux generating conduit arranged in the upper portion of said regenerator vessel above the locus of introduction of the wet desiccant into the regenerator vessel, said reflux generating conduit contacting and partly condensing the vapors in said upper portion and said reflux generating conduit being part of said second conduit.

6. A regenerator in accordance with claim 1 wherein said reboiler comprises an overflow chimney tray and at least one heating coil arranged on top of said tray and below the overflow level.

7. A regenerator in accordance with claim 1 further comprising fifth means for introducing gas into the wet desiccant accumulating on said overflow chimney tray close to the surface of said overflow chimney tray.

8. A regenerator in accordance with claim 1 wherein said regenerator vessel comprises a wide bottom section and a narrower top section, wherein said narrower top section is partly filled with a distillation column packing, and wherein said collector tray is arranged above the center line of said bottom section.

9. A process for drying gas comprising
  a. contacting said gas with a dry desiccant such as to produce a dry gas stream and a wet desiccant stream,
  b. regenerating said wet desiccant stream by,
    aa. passing it into the upper portion of a stripper,
    bb. reboiling desiccant in reboiling means in said stripper,
    cc. withdrawing an $H_2O$ stream from the upper portion of said stripper,
    dd. collecting dry desiccant at an intermediate level on a collecting tray arranged within said stripper below said reboiling means,
    ee. passing the dry desiccant collected on said collecting tray by gravity flow through indirect heat exchange relationship with the wet desiccant before it enters the stripper, and
    ff. recovering the dry desiccant.

10. A process in accordance with claim 9 wherein said gas is natural gas and said desiccant is a glycol.

11. A process in accordance with claim 9 wherein the recovered dry desiccant is recycled to step a.

12. A process in accordance with claim 9 comprising
  a. passing the wet desiccant leaving the contacting step through a flashing section in which entrained gas is removed from the wet desiccant by suddenly lowering its pressure,
  b. passing a portion of the wet desiccant thereafter into indirect heat exchange relationship with the vapors in the top section of said stripper to generate a desiccant reflux in the stripper,
  c. recombining said portion of said wet desiccant with the rest of the wet desiccant,
  d. passing the combined wet desiccant through said indirect heat exchange relationship with the collected liquid dry regenerated desiccant, and
  e. introducing the wet desiccant thereafter into the stripper at the upper section thereof below the area of indirect heat exchange relationship between the wet desiccant stream and the vapors.

13. A process in accordance with claim 1 wherein said gas is natural gas and said desiccant is selected from the group consisting of triethylene glycol and tetraethylene glycol.

14. A process in accordance with claim 1 comprising
  a. recovering said dry desiccant in the bottom portion of said stripper,
  b. passing the still hot dry desiccant through a pump,
  c. passing the dry desiccant from said pump through a cooler, and
  d. passing said dry desiccant into said contacting step.

* * * * *